United States Patent [19]

Neefe

[11] 4,010,496
[45] Mar. 8, 1977

[54] BIFOCAL LENS WHICH POSITIONS WITHIN THE ANTERIOR CHAMBER

[76] Inventor: Charles W. Neefe, P.O. Box 429, Big Spring, Tex. 79720

[22] Filed: Oct. 1, 1975

[21] Appl. No.: 618,382

[52] U.S. Cl. ............................................. 3/13
[51] Int. Cl.² ....................... A61F 1/16; A61F 1/24
[58] Field of Search .............. 3/13, 1; 351/160, 161

[56] References Cited
UNITED STATES PATENTS 3,102,157  8/1963  Gamber ............................. 3/13 X
3,906,551  9/1975  Otter ................................. 3/13

OTHER PUBLICATIONS

"Artiphakia and Aniseikonia" by R. C. Troutman, *American Journal of Ophthalmology*, vol. 56, No. 2, Oct. 1963, pp. 602–639.

*Primary Examiner*—Ronald L. Frinks

[57] ABSTRACT

A bifocal lens implanted in the anterior chamber of the eye having an air space in the upper lens edge to position the lens at the upper edge of the pupil in dilated and constricted state.

1 Claim, 3 Drawing Figures

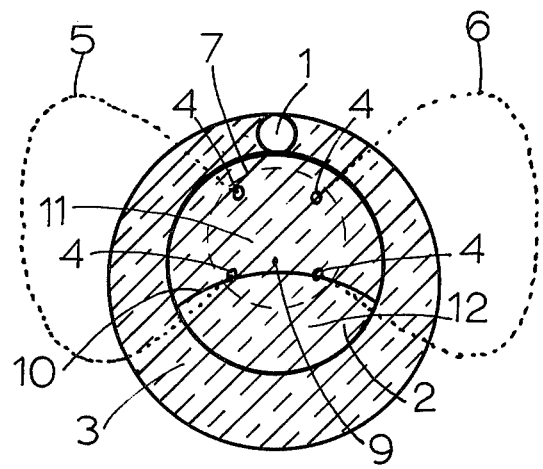
FIG. 1
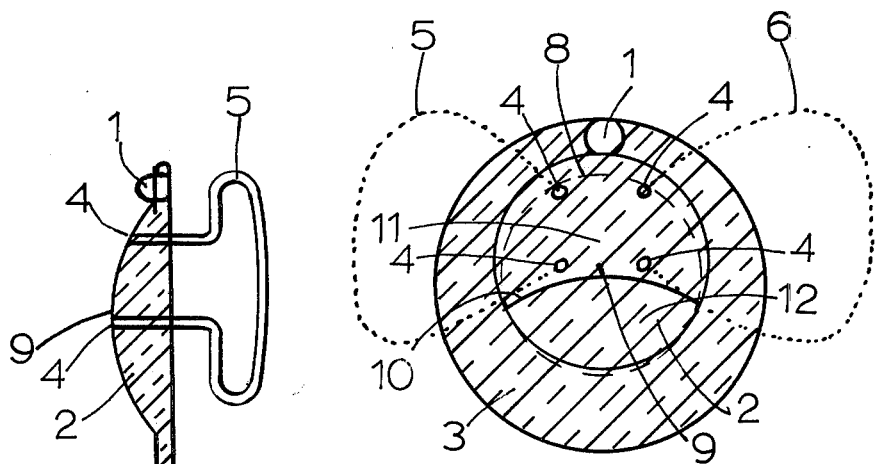
FIG. 3
FIG. 2

BIFOCAL LENS WHICH POSITIONS WITHIN THE ANTERIOR CHAMBER

FIELD OF THE INVENTION

The removal of the crystalline lens after cataract surgery leaves the eye hyperoptic by about nineteen diopters at the plane of the iris. This deficiency in refraction may be replaced by heavy eye glasses or contact lens. The addition of the refractive power at the plane of the iris is desirable to produce a more natural size image and retain unaltered binoculor vision. Strong eye glasses are uncomfortable and produce a greatly enlarged retinal image and distortion resulting in loss of binocular vision in monoculor aphakia. Contact lenses also produce enlargement of the image. If the lens is placed inside the eye a natural size image will result with no enlargement or distortion.

The removal of the crystalline lens leaves the eye with no means to focus at different distances. Bifocal lenses are necessary for all close work.

THE PRIOR ART

Several implant lenses have been tried to achieve these results. An example is U.S. Pat. No. 3,673,616 which discloses an artificial anterior chamber lens which is implanted by inserting it through the pupil and is supported by loops behind the iris and rods in front of the iris. Triangle shaped lens have also been placed in the anterior chamber.

DESCRIPTION OF THE DRAWINGS

For a more complete understanding of the present invention and for further objects and advantages thereof, reference is now made to the accompanying Drawings, in which:

FIG. 1 shows the lens from the front with the pupil constricted and the supporting loops in place behind the iris;

FIG. 2 shows the lens from the front, in place with the loops behind the iris and the pupil dilated;

FIG. 3 shows the lens outside the eye from the side view in section.

DESCRIPTION OF THE PREFERRED EMBODIMENT

The present invention relates to the art of correction of refractive error of aphakics at distant and near vision by placing a bifocal lens in the anterior chamber of the eye. The lenses may be made in three forms: (1) Spherical segments 11 and 12, FIGS. 1 and 2; segment 11 having the distant power and segment 12, the near refractive power. The demarcation line 10, FIGS. 1 and 2 separates the segments 11 and 12. (2) Fresnel optics may be used to reduce the thickness of the lens. (3) Aspheric surfaces having a different curvature or focal length at the center and edge may also be used.

In arriving at the required refractive power for the lens the refractive index of the aqueous must be subtracted from the refractive index of the lens material in air.

The lenses may be made in lenticular form as shown in drawings. FIGS. 1, 2 and 3 show the optical field 2 of the lenticular element and the carrier portion 3. The carrier being approximately 7.5 m/m in diameter prevents subluxation. The air pocket 1 provides buoyancy to make the lens weightless in place. Several small air pockets may be placed around the edge of single vision lenses to achieve a no inertia effect. Bifocals will orientate and position at the upper edge of the pupil if one large air pocket 1, FIGS. 1, 2 and 3 is placed at the upper edge of the lens to provide ballast and prevent rotation. The optical field 2, FIGS. 1, 2 and 3 may be decentered up or down within the carrier flange 3, FIGS. 1, 2 and 3 if desired. The supporting loops 5 and 6 pass through the pupil 7 (FIG. 1) or pupil 8 (FIG. 2) and behind the iris to support and position the lens with the optical center 9 within the central area of the pupil 7 or 8. The loop support holes 4, FIGS. 1, 2 and 3 are placed 2 m/m apart near the upper edge of the optical field 2, FIGS. 1, 2 and 3.

The bifocal functions as follows: FIG. 1 shows the pupil 7, FIG. 1 constricted as in bright sunlight. A small portion of near segment 12, FIG. 1 occupies the pupil area. Near vision would be impossible in bright light. Distant vision is excellent outside in bright light. The optical center 9, FIGS. 1 and 2 is near the pupil center. FIG. 2 shows the pupil dilated and a larger portion of the near segment 12 occupying the pupil area. Reading and close vision are now possible under lowered illumination. This great increase in near segment pupil area is due to the upward movement of the lens as the pupil dilates and the ballasted lens floats upward. The upper support loop holes 4, FIG. 2 are positioned at the upper edge of the dilated pupil.

The traditional reading glasses are required only outside in bright light at which time bifocal sunglasses should be worn.

Various modifications can be made without departing from the spirit of this invention or the scope of the appended claims. The constants set forth in this disclosure are given as examples and are in no way final or binding. In view of the above, it will be seen that the several objects of the invention are achieved and other advantages are obtained. As many changes could be made in the above constructions and methods without departing from the scope of the invention, it is intended that all matter contained in the above description shall be interpreted as illustrative and not in a limiting sense.

What is claimed is:

1. An implantable bifocal intra-ocular lens for the anterior chamber of the eye comprising a lenticular shaped body having a transparent optical portion provided with an upper distant refractive segment and a lower near refractive segment, lens support means extending outwardly and rearwardly from said body for positioning through the pupil and posterior to the iris with said body to be positioned anterior to the iris, at least one floatation void at the upper edge of said body whereby when said lens is implanted in the eye it will be positioned at the upper edge of the pupil when the pupil is either dilated or constricted and said near refractive segment will be within the pupil when it is dilated and said near refractive segment will be substantially below the pupil when it is constricted.

* * * * *